United States Patent [19]

Walker

[11] 4,236,820
[45] Dec. 2, 1980

[54] CUVETTE AND STANDARD HOLDER FOR OXIMETERS

[75] Inventor: Terence Walker, East Aurora, N.Y.

[73] Assignee: American Optical Corporation, Southbridge, Mass.

[21] Appl. No.: 11,460

[22] Filed: Feb. 12, 1979

[51] Int. Cl.³ .................... G01N 21/55; G01N 21/13; G01N 33/72
[52] U.S. Cl. .................................. 356/41; 356/42; 356/244
[58] Field of Search ................. 356/39, 40, 41, 244, 356/42

[56] References Cited

U.S. PATENT DOCUMENTS

| | | | |
|---|---|---|---|
| 3,296,922 | 1/1967 | Goldberg | 356/51 |
| 4,040,747 | 8/1977 | Webster | 356/244 |

*Primary Examiner*—Vincent P. McGraw
*Attorney, Agent, or Firm*—Jeremiah J. Duggan; Alan H. Spencer

[57] ABSTRACT

A mechanism for carrying a calibration standard and receiving a cuvette containing a blood sample to be tested is disclosed. The mechanism permits convenient shifting to either the test position or calibration position.

5 Claims, 8 Drawing Figures

CUVETTE AND STANDARD HOLDER FOR OXIMETERS

BACKGROUND OF THE INVENTION

1. Field of the Invention

This invention relates to improvements in apparatus for evaluating the oxygen saturation of blood and relates more particularly to a class of instruments known as reflectance oximeters. In such instruments an electro-optical system functions to cause light at two preselected different wavelengths to radiate a whole blood sample contained in a cuvette.

2. Discussion of the Prior Art

As is known in the art, one of the two wavelengths selected to be diffusely reflected equally by the oxyhemoglobin and reduced hemoglobin in the blood. The other wavelength of light is selected such that it is reflected efficiently by the oxyhemoglobin and is strongly absorbed by the reduced hemoglobin. The oximeter then compares the values of reflected light at the predetermined wavelengths and according to known equations computes the oxygen saturation of the blood.

One such instrument for the measurement of oxygen saturation in the blood is described in detail in U.S. Pat. No. 3,296,922, assigned to the Assignee of the present application. This patent describes the electro-optical system for determining the relationship of saturations in the blood of the hemoglobin at wavelengths of 660 and 805 millimicrons wherein the light source is an incandescent lamp and various filtering means are used to accomplish the selected light wavelengths for irradiation.

The procedure by which reflected oximetry may be performed is described in U.S. Pat. No. 3,177,757 also assigned to the assignee of the present invention.

With the advance of the electronic arts and the development of light-emitting diodes, it has become advantageous to use independent separate light sources for the preselected wavelengths of light used to irradiate the selected blood samples. The inclusions of such improvements in the art of reflective oximetry are discussed in U.S. Pat. No. 3,647,299. In U.S. Pat. No. 3,647,299, drive circuits for the utilization of light-emitting diodes in reflective oximetry are described in U.S. Pat. No. 3,902,806, both of these identified patents are assigned to the Assignee of the present invention. One of the more recent advances in reflective oximetry has occurred in the area of the development of a disposable cuvette for the use of the clinician in making the oxygen saturation determinations. Since the disposable cuvette has eliminated the need to clean the cuvette including sterilization, the technician may now evaluate a number of blood samples in rapid succession by merely cycling through each sample in its own disposable cuvette.

The present invention is directed to improving the mechanism of the reflective oximeter to take most advantageous use of the disposable cuvette and flexibility of its operation and coordinate that with improving the speed and ease with which oxygen saturation measurements may be made in the oximeter.

SUMMARY OF THE INVENTION

In accordance with the features of the present invention, there is provided mechanism for facilitating the receiving of a cuvette into a station in the measuring apparatus and moving that cuvette station into registry with the optical aperture of the instrument to affect a measurement of a sample within the cuvette.

There is additionally included within the same mechanism for receiving the cuvette, a reflectance standard which is alternatively disposed over the optical aperture for calibration of the instrument when actual measurements of the cuvette sample are not being made. The mechanism includes arm means which is journaled for rotary motion in a plane generally horizontally of the top of the oximeter instrument cabinet and to at least the two positions, with either the reflectance standard or the cuvette mounting station oriented perpendicularly over the optical aperture. The arm means includes platform means in which is located the cuvette station and the reflectance standard station. This platform means is disposed in the arm means some distance from the journal of the arm and is oriented adjacent the optical aperture of the instrument so as to permit the cuvette station and reflectance standard to be rotated into position above the optical aperture. The platform in its function as orienting means is loosely retained in the arm so that the platform may bear directly on the oximeter apparatus adjacent the optical aperture. The platform thus contains means for orienting the platform within the arm with respect to the vertical center of the optical aperture to ensure placement of the reflection standard or cuvette directly on the vertical center of the optical aperture. Included also on the platform are leg means disposed on the underside of the platform, the length of the legs is adjusted or adapted so as to determine a reference plane in the platform which is parallel to the plane of the optical aperture when the legs are bearing on the oximeter apparatus adjacent the optical aperture. As can be thus recognized, by such as the leg means, the platform which contains the cuvette station and the reflectance standard is oriented precisely in the horizontal plane with respect to the optical aperture as is necessary for repeated, accurate measurements either of standard reflectance or reflectance of the blood sample within the cuvette. The platform, at the cuvette station, contains a bearing surface which generally surrounds the area where the cuvette is supported. This bearing surface is disposed in a plane at a predetermined distance from, and parallel to, the reference plane as should be recognized as necessary to ensure orientation of the cuvette relative of the optical aperture and similarly as the reflectance standard. Retaining means is disposed in the platform adjacent the cuvette station for detachably securing the cuvette on the bearing surface at the cuvette station.

The light reflection standard is disposed on the platform adjacent the cuvette station and oriented in the platform as to be substantially equidistant from the journal of the arm containing the platform as the cuvette station of the cuvette. Accordingly, when the arm is rotated, the reflection standard or the cuvette station and cuvette are rotated into position oriented with respect to the vertical axis of the optical aperture so that accurate reflectance measurements may be taken.

Further advantages and features of the present invention will become apparent from reference to the detailed description of a preferred embodiment below and the appended drawings.

DESCRIPTION OF THE PREFERRED EMBODIMENT

Figure 1:
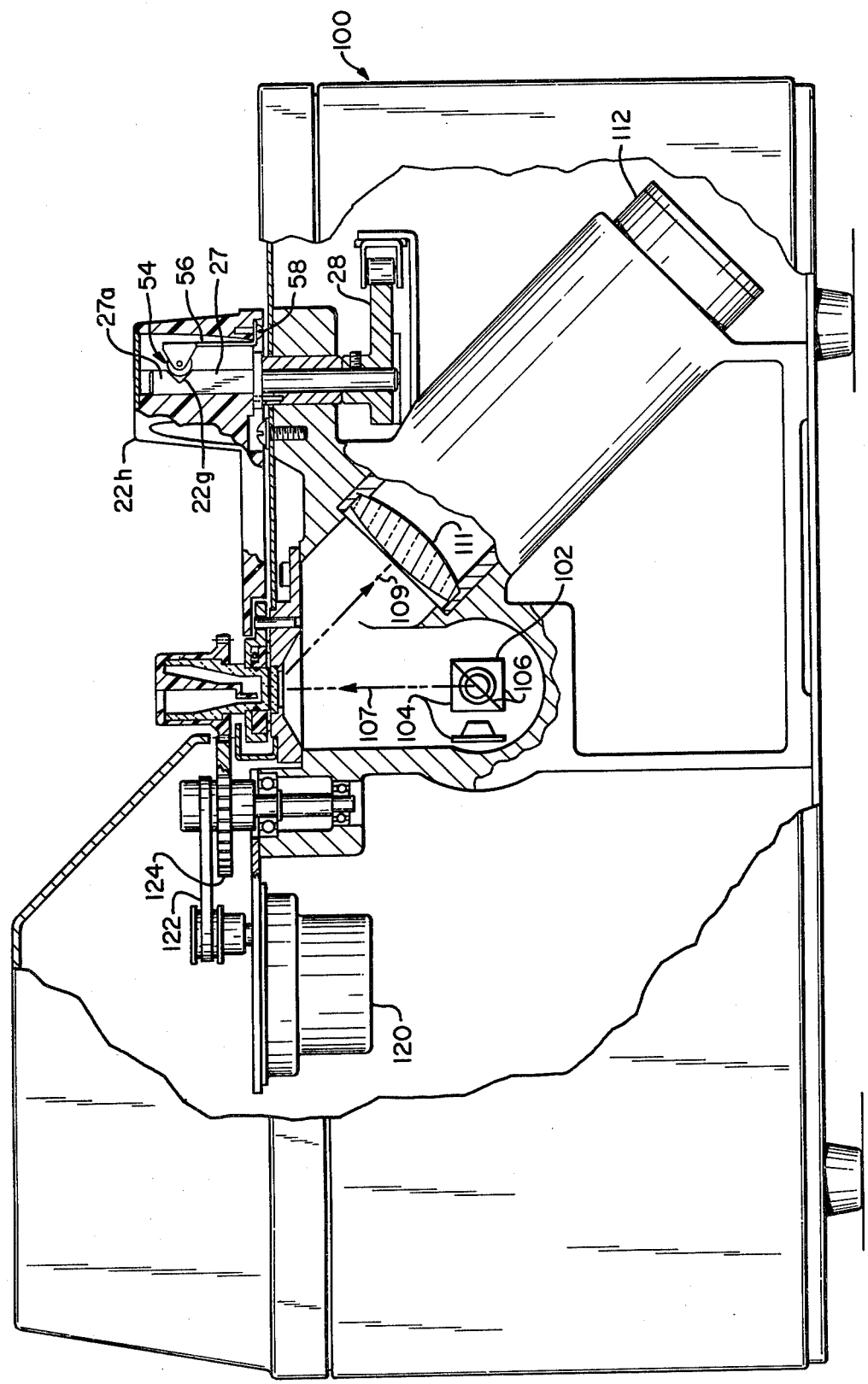
FIGS. 1 and 1a are a side views, partially in section, of oximetry apparatus including the present invention.
Figure 1A:
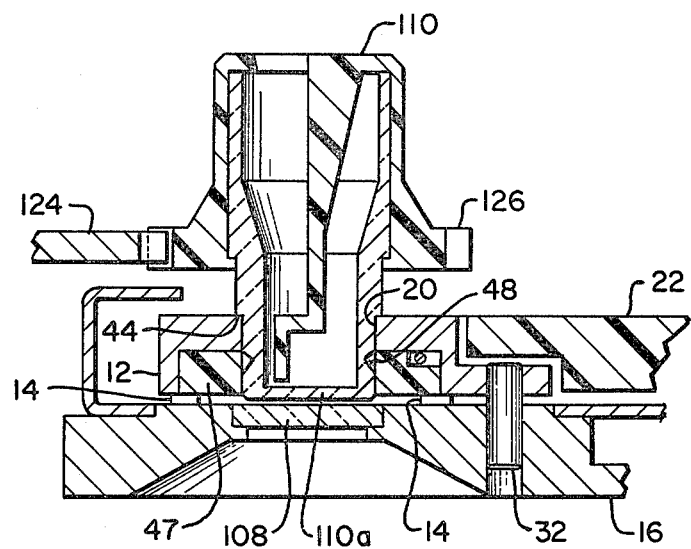

Referring now to the drawings and FIG. 1 in particular, reference numeral 100 indicates an oximeter of the reflectance type within which the present invention is embodied. Within the body of the oximeter 100 is the light source 102 for generating the various predetermined light wavelengths utilized in the reflection measurement. In the present embodiment, light-emitting diodes 104 are utilized. These are located on axes approximately 90° from each other and, through mirrors such as 106, the light is reflected to a common axis and projected up to optical aperture 108 in the instrument wherein the light is reflected off of either the standard or the cuvette (illustrated at 110). The light being reflected from the cuvette or standard, whichever is in position, is reflected along optical axis 109 through various appropriate lenses 111 to a detector 112. The previously cited patents illustrate and describe in greater detail the apparatus thus described. Through electronic circuitry, not shown but of the type disclosed in the aforementioned patents and well-known in the art, the various intensity levels of the selected light wavelengths may be determined. According to the measurements, a digital readout 116 indicates the degree of oxygen saturation of a particular sample contained within a cuvette 110.

As is known in the art, during the process of reflective oximetry, it is necessary that the blood sample be continually stirred. Utilizing a cuvette of the type shown in U.S. Pat. No. 3,947,122 and illustrated at reference numeral 110, stirring can be continually affected through the utilization of a motor 120 operating through a belt drive 122 to a gear drive 124. Gear drive 124 interconnects with the geared portion of the cuvette assembly 126 which is illustrated as reference numeral 9 on the referred U.S. Pat. No. 3,947,122. As will be subsequently explained in the present embodiment, it is advantageous that motor 120 be activated whenever the cuvette is in the operative position for reflectance measurements. A suitable means for doing this is subsequently described.

Figure 2A:
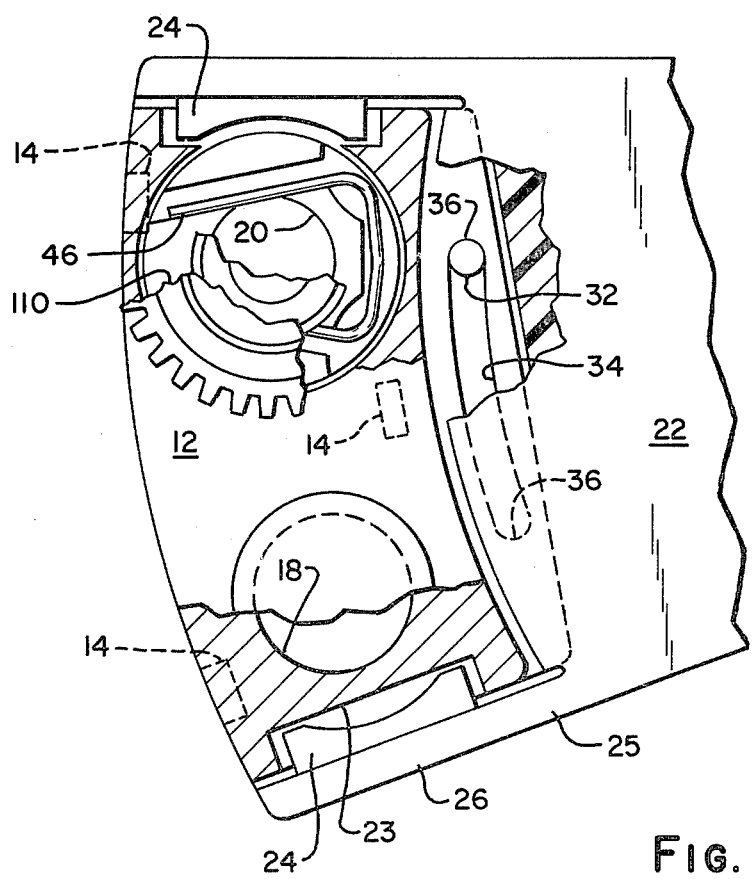
FIGS. 2 and 2a are top views, partially in section, of the appartus of FIG. 1.
Figure 2:
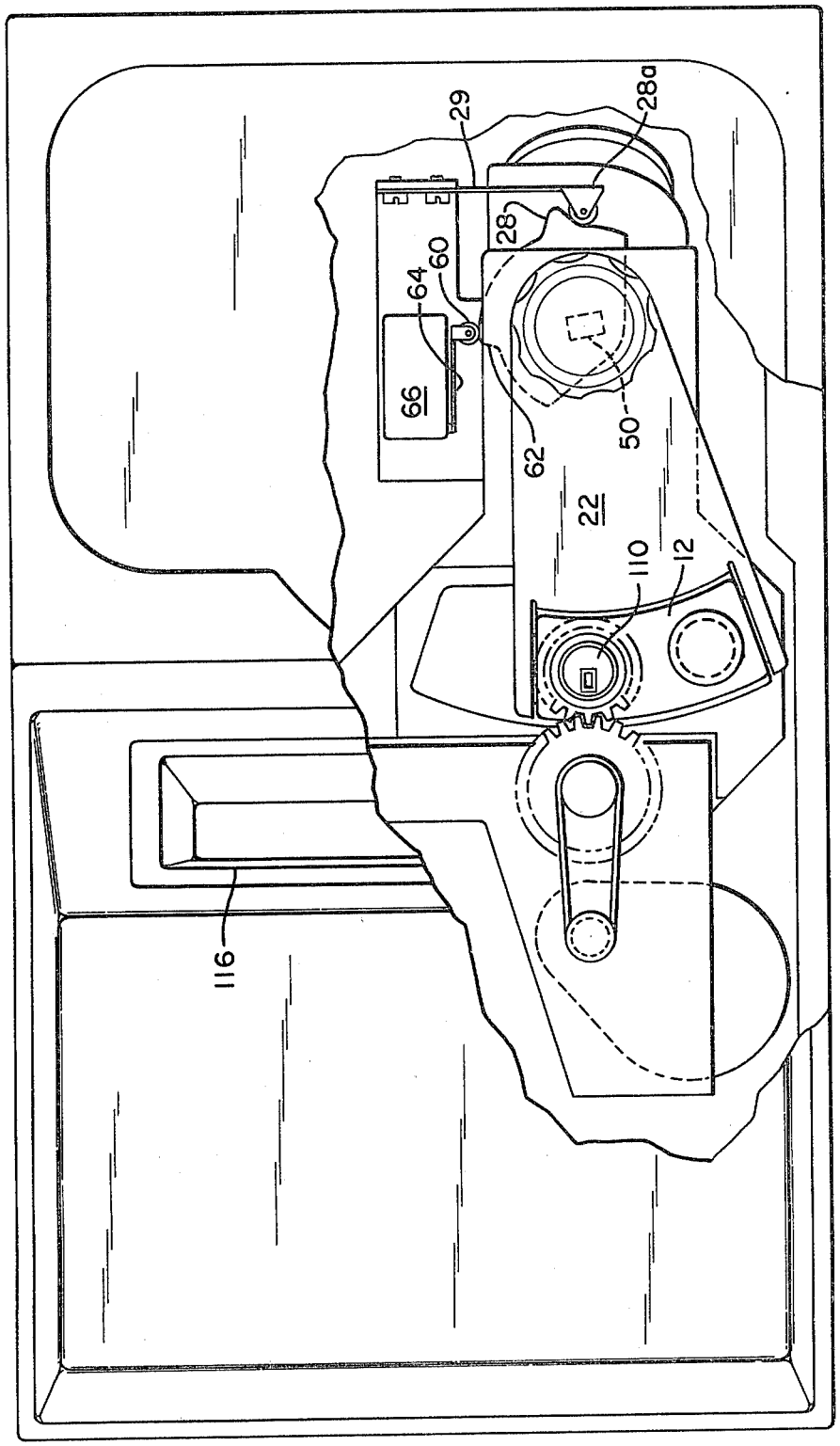
Figure 3A:
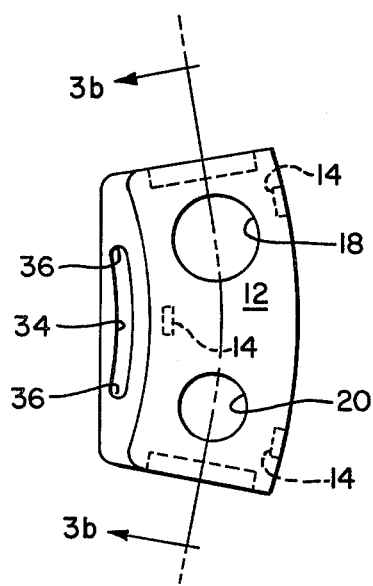
FIGS. 3a and 3b are top and side views of the control arm of the apparatus of FIGS. 1 and 2.
Figure 3B:
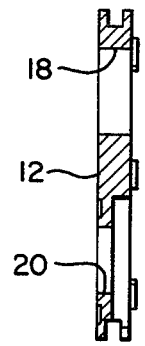

A principal element in the oximeter mechanism for cycling the disposable cuvettes 110 through the measuring cycle of the oximeter 100 is platform 12 (illustrated also in FIGS. 2, 3a, and 3b. In the present embodiment, the platform is machined from stainless steel and includes legs 14 so as to rest on housing 16 of the optical aperture 108 within the instrument 100. Two stations are machined into the platform 12, one for the fixed glass reflection standard 18 and bore 20 to form the cuvette (110) station. As may be best seen in FIG. 3, platform 12 is somewhat trapezoidal in shape actually describing a segment of an arc, the center of which is the journal point or pivot of the control arm 22 within which platform 12 is disposed. As may be seen, the reflection standard station 18 and the cuvette station 20 are disposed on a common arc within platform 12 such that when the platform is rotated around the center of that arc, either of the two stations may be brought into registry with the optical aperture for the performance of the reflection measurements.

Figure 4A:
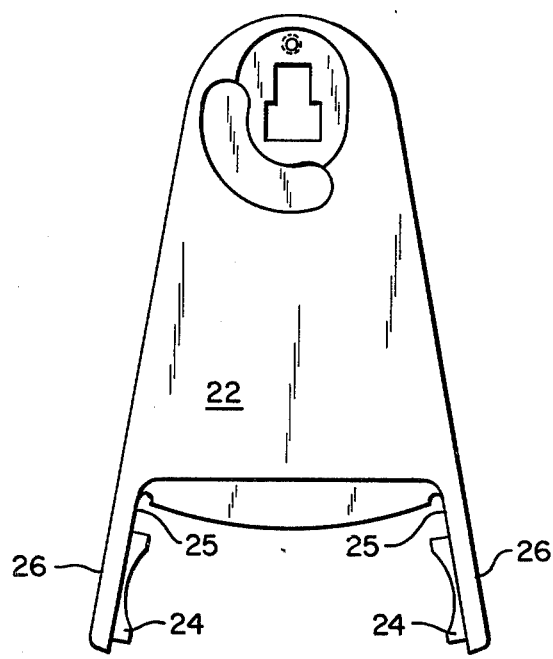
FIGS. 4a and 4b are top and side views of the platform means of the apparatus of FIGS. 1 and 2.
Figure 4B:
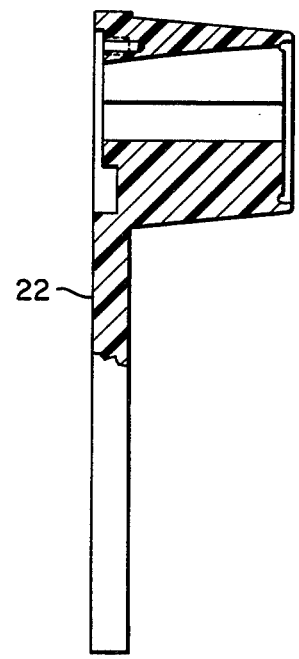

Referring now to FIGS. 1, 2 and 4, the control arm 22 is illustrated. Platform 12 is loosely retained in control arm 22 by two shoes 24 which protrude from the inner surface 25 of the control arm fingers 26. Arm 22 is journaled on a shaft 27, the other end of which is fixed to cam 28 which through spring 29 forces control arm 22 toward one of the two measuring positions (cuvette or reflection standard).

Cooperating with the platform 12 to assure precise alignment of either the cuvette or reflection standard to the center of the optical aperture 108 is pin 32 extending upwardly of the instrument housing 100 so as to engage a slot 34 in platform 12. The slot 32 is arcuate in form and concentric with the arc upon which the reflection standard and cuvette mounting stations are placed (e.g. centered on shaft 27).

Operation of the control arm 22 in either direction urges platform 12 to rotate from one measuring position to the other. Fingers 26 bear on platform 12 at their inner surfaces 25. Pin 32 slides in slot 34 until reaching one of the two ends 36 thereof. Each end 36 is located such that one or the other of the measuring stations are precisely aligned over the optical aperture 108. When arm 22 traverses the extent of its normal movement, its motion is limited by pin 32 and slot 34. Cam 28, operating in conjunction with cam driver 28a, is attached to spring 29 and urges arm 22, and thus platform 12, in one of the two movement directions. In this manner, pin 32 remains firmly seated at the appropriate slot end 36 during reflectance measurement of either the standard or the cuvette. It may be thus seen that precise optical alignment in both the vertical direction and the horizontal direction are accomplished by the movement of platform 12 over the window housing 16.

To ensure that cuvette 110 is precisely restrained in platform 12 to preserve the vertical alignment of the cuvette and horizontal alignment of the reflectance surface thereof 110a, cuvette 110 is restrained against the bearing surface 42 on platform 12 through spring pressure. Cuvette 110 includes seating surface 44 on the underside thereof which cooperates with bearing surface 42 to preserve the parallel relationship of the planes of these surfaces with the plane of platform 12 as established through legs 14. A horseshoe-shaped spring 46 is disposed in a cuvette-retaining disc 47, spring 46 acts against the lower angular surface of angular groove 48 in cuvette 110 to urge cuvette 110 into firm seating arrangement on platform 12. Spring 46 also allows cuvette 110 to be easily inserted or withdrawn into the mounting station at the beginning and termination of measurement operations.

In a preferred form, control arm 22 is detachable from the shaft 27. Rotary location of the arm 22 on shaft 27 is accomplished by making the shaft segment 27a rectangular in cross-section which, in turn, is recieved in a complementary slot in main handle 22h of arm 22. Arm 22 may be oriented vertically on shaft 27 by means of a cam follower 54 (a roller) attached to the interior portion of the handle 22h under spring tension 56. An angular groove 27g is cut into shaft 27 such that upon placement of handle 22h on segment 27a, cam follower 54 seats on groove 27g.

In the illustrated embodiment, control arm 12 is made of a molding grade Delrin plastic. Due to the resilient nature of the plastic material, fingers 26 may be spread slightly such that shoes 24 are released from retaining slots 23 and platform 12. It is desirable that platform 12 be detachable from the control arm to facilitate cleaning and maintenance of the operational parts thereof. Control arm 22 may be manufactured of other materials. Should such materials not exhibit the requisite resiliency for platform 12 to be easily removable therefrom, one of the fingers 26 may be operably moveable with respect to the arm, per se, and perhaps spring-loaded about a pivot to permit actuation of the fingers and removal of the platform.

As previously indicated, it is desirable that starting motor 120 be operated when the cuvette 110 is rotated in platform 12 on arm 22 so as to be in a measuring position over the optical aperture 108. This may be accomplished by the inclusion of a second cam surface 60 on cam 28 attached to shaft 27. Accordingly, when the cam 60 is rotated into position, cam follower 62 is deflected such that the operating arm 64 to which it is attached may actuate microswitch 66. Switch 66 may be operably electrically connected to motor 120 so that the motor is turned on when the operating arm 64 is deflected. Accordingly, when the control arm 22 is rotated such that reflection standard is in the measuring position, the control arm 64 of switch 66 is released and starting motor 120 is shut off.

This invention may be embodied in yet other specific forms without departing from the spirit or essential characteristics hereof. Thus, the present embodiments are to be considered in all respects as illustrative and not restrictive and the scope of the invention being indicated by the appended claims rather than by the foregoing description. All changes which come within the meaning and range of equivalency of the claims are, therefore, intended to be embraced therein.

I claim:

1. In apparatus for reflective oximetry for determination of the percentage of oxygen saturation of whole blood wherein a sample of blood is placed in a cuvette and supported on means such that light of known wavelengths may be directed through an optical aperture onto the optical surface of the cuvette and the light reflected therefrom is measured and compared to reflected light from a reflectance standard and the percentage of oxygen concentration calculated therefrom, the improvement comprising:

apparatus for supporting said cuvette and said reflectance standard for light reflection measurements including;

arm means journaled for rotary motion in a substantially horizontal plane on said oximetry apparatus to at least two positions contiguous said optical aperture;

platform means having a cuvette station and a reflectance standard station disposed in said arm means displaced from said journal and relatively adjacent said optical aperture, said platform being loosely retained in said arm so as to bear directly on said oximetry apparatus adjacent said optical aperture;

means for orienting said platform means in said arm with respect to the vertical center of said optical aperture;

leg means disposed on the underside of said platform means, said leg means adapted to determine a reference plane in said platform parallel to the plane of said optical aperture when said legs bear on said oximetry apparatus;

a bearing surface surrounding said cuvette station, said bearing surface disposed in a plane at a predetermined distance from and parallel to said reference plane;

cuvette retaining means disposed in said platform adjacent said cuvette mounting station for seating said cuvette on said bearing surface at said mounting station; and a light reflection standard disposed in said platform means adjacent said cuvette station and substantially equidistant said journal as said cuvette station.

2. Apparatus according to claim 1 wherein said cuvette retaining means includes means for detachably seating said cuvette on said bearing surface.

3. Apparatus according to claim 2 wherein said means for detachably seating said cuvette on said bearing surface includes spring means cooperating with spring-receiving means on said cuvette to retain said cuvette on said bearing surface.

4. Apparatus according to claim 1 wherein said arm means includes a bifurcated end portion adapted to detachably retain said platform means therebetween.

5. Apparatus according to claim 4 wherein said oximetry apparatus includes an upstanding pin located proximate said optical aperture and said platform means contains an arcuate slot, said slot having ends being centered on the radii from said arm journal of said cuvette station and said reflection standard station when said platform is retained in said bifurcated arm.

* * * * *